(12) United States Patent
Tims et al.

(10) Patent No.: US 6,358,224 B1
(45) Date of Patent: Mar. 19, 2002

(54) IRRIGATION SYSTEM FOR ENDOSCOPIC SURGERY

(75) Inventors: Jerry L. Tims, Azle; Andrew F. Ditterline, Arlington, both of TX (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 09/405,684

(22) Filed: Sep. 24, 1999

(51) Int. Cl.[7] ............................................... A61M 3/00
(52) U.S. Cl. ......................................... 604/30; 604/246
(58) Field of Search ............................. 604/27, 30, 31, 604/32, 33, 34, 35, 36, 131, 246, 248, 249, 250

(56) References Cited

U.S. PATENT DOCUMENTS

| | | |
|---|---|---|
| 5,447,414 A | 9/1995 | Nordby et al. |
| 5,542,918 A * | 8/1996 | Atkinson ..................... 604/27 |
| 5,545,012 A | 8/1996 | Anastos et al. |
| 5,549,456 A | 8/1996 | Burrill et al. |
| 5,672,051 A | 9/1997 | Forgue et al. |
| 5,725,357 A | 3/1998 | Nakazeki et al. |
| 5,736,823 A | 4/1998 | Nordby et al. |
| 5,868,175 A | 2/1999 | Duff et al. |
| 6,176,847 B1 * | 1/2001 | Humphreys, Jr. et al. .. 604/246 |

* cited by examiner

Primary Examiner—Manuel Mendez

(57) ABSTRACT

An irrigation system for use during endoscopic or minimally invasive surgery is shown. Both vacuum and a pressurized irrigation fluid are continually provided to a trumpet valve for immediate use during surgery. A pump that provides the pressurized irrigation fluid has a reusable motor, but a disposable head that can be replaced between procedures. A control circuit automatically reduces the voltage being supplied to the pump if there had not been a request for irrigation fluid for a first time period. If a second time period, which is longer than the first time period, passes and (a) there is no demand for irrigation and (b) the voltage to the pump has not been reduced, either the voltage to the pump will be reduced or the pump shut OFF. The irrigation system is provided in kit form with parts having to be replaced between procedures contained therein.

14 Claims, 6 Drawing Sheets

IRRIGATION SYSTEM FOR ENDOSCOPIC SURGERY

FIELD OF THE INVENTION

This invention relates generally to an irrigation system to be used during surgery and, more particularly, to an irrigation and vacuum system for use in conjunction with endoscopic or minimally invasive surgery.

BACKGROUND OF THE INVENTION

Laparoscopic surgery was first performed in France in 1987 and in the United States in 1988. Since that time laparoscopic surgery, also known as minimally invasive or endoscopic surgery, has grown at a phenomenal rate. Many procedures that previously used open surgery techniques are now done using a laparoscopic approach.

While laparoscopic surgery initially developed with the removal of gall stones, laparoscopic surgery is now used for many other surgical procedures including hernia repair, appendectomy, pediatric, gynecological, genitourinary, bowel, colorectal, gastroduodenal, and vascular surgery, just to name some examples. Laparoscopic or minimally invasive surgery is the latest rage in new surgery techniques. By use of laparoscopic surgery, infection and trauma for the patient is reduced. The patients are able to go home much earlier and have much less effect from the surgery. The pain and suffering normally associated with surgery is greatly reduced. Laparoscopic surgery is truly the wave of the future in surgical techniques.

In normal laparoscopic surgery, a trocar and cannula are inserted through the esophagus, around muscle and other tissue, and into a body cavity where the surgeon is to perform the surgical procedure. As the surgical procedure is being performed, it is necessary to remove the fluids from the body cavity that may interfere with the ability to physically see what is occurring. As would occur in open surgery, laparoscopic surgery needs to provide irrigation to the area where the procedure is being performed and suctioning to remove the irrigation fluid as well as the body fluids that interfere with the ability to visually see what is occurring.

Using an appendectomy as an example of the surgery that is being performed laparoscopically, typically there would be (a) a puncture for the endoscope, (b) a puncture for the appendix extractor, and (c) a puncture for the insertion of the surgical instruments. It is necessary for the surgeon to be able to see through the endoscope what is occurring in the body cavity. The providing of irrigation fluids to the body cavity and the removal of those fluids is necessary for the successful performance of the appendectomy.

In the past, irrigation is normally provided through a trumpet valve via one of the punctures to the body cavity. The trumpet valve is connected to a source of (a) saline solution for irrigation purposes and (b) vacuum for extraction of the irrigation fluid and body fluids. Depending upon which portion of the trumpet valve is pushed, either irrigation or vacuum is provided. However, during long periods of non-use, neither irrigation nor vacuum will be provided to the patient.

Typically, the irrigation fluid is provided under pressure by means of a pump to the trumpet valve. It is important to the surgeon to have pressurized irrigation fluid immediately available with essentially no delay upon pushing the trumpet valve. The surgeon does not want to have to reach and flip other switches, such as hand or foot switches, or push other buttons other than pushing the trumpet valve itself. In other words, the surgeon wants to push one button on the trumpet valve to provide irrigation fluid and push another button on the trumpet valve to remove the irrigation fluid and body fluids. When neither are pushed, neither irrigation fluid nor a vacuum are being provided to the body cavity of the patient. The surgeon wants either irrigation fluid or vacuum to be available instantaneously upon demand. Moreover, providing a separate switch has the additional disadvantage of increased controls and complexity of the system plus additional expense.

In the past, pumps that would provide the irrigation fluid would have to be switched ON to provide the fluid and then turned OFF. When the pump was switched ON, there would be a delay of several seconds before the irrigation fluids are provided under pressure. This delay is disadvantageous and unacceptable to the surgeons. To avoid the foregoing disadvantage, the pump could be designed to run continuously. However, if the pump is left ON continuously and no fluids are flowing so the pump is operating in a "deadhead" condition, the pump has a tendency to overheat as it constantly rotates at a relatively high speed without the fluids flowing through the pump which provide cooling for the pump. Excessive heating of the pump affects the reliability of the pump, can cause hot fluid to be supplied to the patient, and can even blow off the connections as pressure builds. Therefore, in systems with continuously running pumps, some type of external cooling must be provided for the pump, which is a problem when performing laparoscopic surgery.

Consequently, it would be advantageous to provide a system which can supply irrigation instantaneously on demand without requiring a separate ON/OFF switch and without resulting in overheating of the pump. Also in the past, a tremendous expense incurred in laparoscopic surgery is the replacement of the entire system between procedures. Normally after a laparoscopic surgery technique is performed on one patient, the entire irrigation system (including the pump and all valving associated therewith) is thrown away and replaced with a new laparoscopic irrigation system before a new procedure is performed on a new patient.

The motor portion of the pump, including the windings and coils, is fairly expensive. If the windings and coils portion of the pump can be reused, this could save a considerable amount of money. The irrigation fluid itself is sterile and does not contaminate the pump. If backflow from the trumpet valve is prevented, it may be possible to reuse either a portion or even the entire pump. By the present invention, it is found that a portion of the pump can be replaced and still save the major expense that may be incurred by replacing the entire pump.

SUMMARY OF THE INVENTION

The present invention overcomes the foregoing disadvantages by providing a pump that can be switched from one operating condition to another operating condition and still not be turned OFF. By switching to a second operating condition, the pump can be ready to instantaneously deliver irrigation fluid under pressure and still avoid the problem of overheating as will be discussed further hereinbelow in conjunction with the present invention.

In endoscopic surgery, such as laparoscopic surgery which is provided through the abdomen, a saline solution is normally provided through a trumpet valve and a cannula into a cavity of the patient's body. The saline solution is pumped by a positive pressure pump. By pushing one button on the trumpet valve, the saline solution is pumped from the pump into the cavity of the patient's body. By releasing the first button on the trumpet valve and pushing the second button, the same cannula is now connected to a source of vacuum. The source of vacuum will suck the saline solution and any body fluids at the end of the tube in the cavity of the patient's body back toward the vacuum source with the fluids being collected in a vacuum cannister.

So that the entire system does not have to be thrown away when switching from patient to patient, the pump has been made partially disposable. The head of the pump that includes the impellers is made from a medical grade, yet disposable, plastic. By a simple hand twisting action, the head of the pump is connected to the body of the pump. The body of the pump may be used repeatedly.

Because the pump normally operates at 12 volts DC, if it continues to operate at that voltage at a no-load or deadhead condition, the pump will overheat. To eliminate the problem of overheating, if fluid does not flow through the pump for a predetermined time, the voltage being applied to the pump will be reduced. The reduced voltage reduces the speed of the pump and hence the friction created by the impellers continuing to circulate the fluid in a deadhead condition. This reduced speed reduces almost exponentially the amount of heat being generated by the pump. Therefore, at the reduced voltage, the pump does not create excess heat, but at the same time maintains saline solution under pressure at the trumpet valve ready for instantaneous delivery to the patient if requested by the surgeon. A timing circuit is provided in the controls for the voltage source. After a predetermined time interval during which no fluids have been requested, the pump will automatically switch to a lower voltage.

To make the electronics portion of the power supply failsafe, an override or "crowbar" circuit is included. The override circuit automatically reduces the voltage being applied to the pump if the first time interval, plus an additional time interval has passed and the voltage of the pump has not been reduced. The additional timing circuit, or crowbar circuit, overrides the prior electronic controls for the power supply to reduce the voltage being applied to the pump.

As a safety when the disposable portion is reused, additional check valves may be included to prevent backflow from the trumpet valve back to the head of the pump. By simply replacing the check valve and the downstream hoses, the disposable head of the pump could be used a few times without danger of infection.

The timing portion of the circuit is simply used to reduce the voltage being applied to the motor during periods of non-use and, hence, the speed of the motor after a period of nonuse of the motor to deliver an irrigation solution to the patient. A failsafe circuit is included in the event of a failure by the electronics.

DESCRIPTION OF THE PREFERRED EMBODIMENTS

Figure 1:
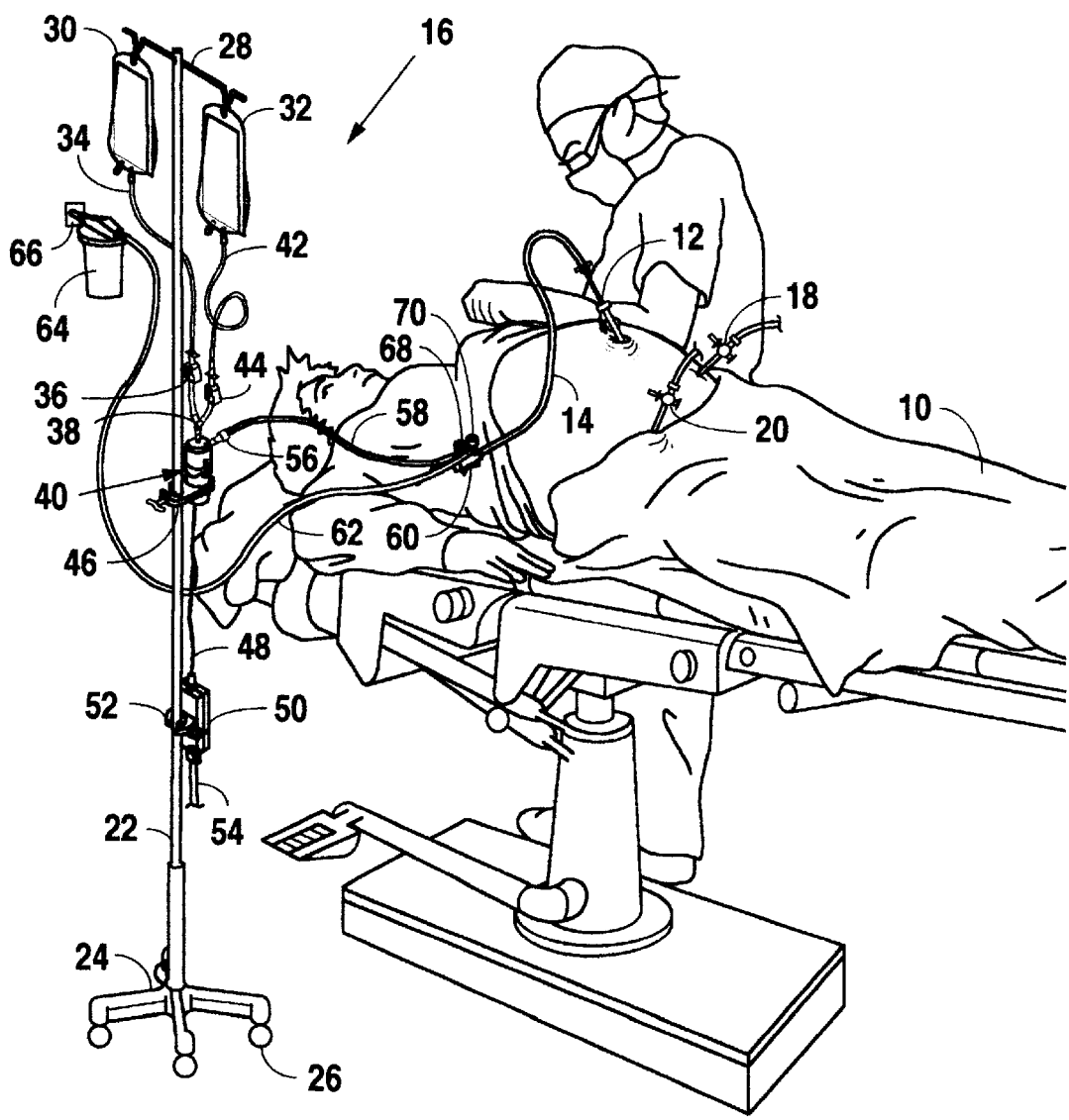
FIG. 1 is an environmental perspective view showing a new irrigation system being used during laparoscopic surgery.

Referring to FIG. 1 of the drawings, there is shown an environmental view of the irrigation system as embodying the present invention being used during a laparoscopic surgery procedure on a patient 10. Laparoscopic surgery is sometimes used synonymously with the general terms of minimally invasive surgery or endoscopic surgery. During laparoscopic surgery, the patient 10 normally has three puncture wounds through which cannulas or sleeves are inserted to allow access to the body cavity. For purposes of illustration, assume an appendectomy is being performed, cannula 12 allows for the connection to an endoscope (not shown) and to the delivery line 14 of the present irrigation system represented generally by the referenced numeral 16. Cannula 18 provides for the appendix extractor (not shown) and cannula 20 allows for the insertion of the instruments (not shown) while performing the appendectomy. An additional cannula (not shown) could be inserted in the upper abdomen to simplify the intra corporeal knotting, but is not absolutely necessary. Also, the delivery of the irrigation fluids may be through some other cannula other than cannula 12, but is being illustrated in conjunction with cannula 12 for illustrative purposes.

An IV pole 22 is provided on a base 24 mounted on rollers 26. At the top of the IV pole 22 is contained a crossbar 28 for supporting intravenous fluid (IV) bags 30 and 32 thereon. The IV bags 30 and 32 are normally filled with a saline solution that can be used to irrigate and/or flush out internal cavities to remove body fluids so that a doctor can see what is occurring during the operation. Also, the IV fluids are used to wash or clean the wound area. IV bag 30 is connected through tube 34, tubing clamp 36 and Y connection 38 to pump 40.

Likewise, IV bag 32 is connected through tube 42 and tubing clamp 44 to Y connection 38 of pump 40. Normally, only one of tubing clamps 36 or 44 is open at a time allowing flow from either IV bag 30 or IV bag 32.

Pump 40 is attached to IV pole 22 by means of pump clamp 46. Pump 40 receives power through power connection 48 of power supply 50. Power supply 50 is mounted to the IV pole 22 by power supply clamp 52. The power being supplied by power supply 50 is typically 12 volts DC. Power supply 50 takes ordinary 60 cycle, 110 volt, AC power from a wall outlet through power cord 54 connected to power supply 50. In foreign countries, the power being supplied through power cord 54 may be 50 cycle AC versus 60 cycle AC. In either event, the power supply 50 will convert the AC power to 12 volts DC for delivery through the power connection 48 to the pump 40. As will be described hereinbelow, the power supply 50 also reduces the 12 volt DC being delivered through power connection 48 to the pump 40 if there has been no demand for power for a predetermined time interval.

From the pump 40, IV fluids from either IV bag 30 or 32 will flow through the pump 40, check valve 56, and irrigation line 58 to trumpet valve 60. Trumpet valve 60 is also connected through a vacuum line 62 and a vacuum cannister 64 to a vacuum source 66. Every major hospital has a vacuum source 66 that is readily available in the operating room. The vacuum cannister 64 is a standard vacuum cannister that collects any fluids being drawn out of the patient 10 through trumpet valve 66.

Trumpet valve 60 has an irrigation button 68 that may be pushed by the physician when irrigation fluids from either IV bag 30 or 32 need to be delivered to the patient 10. Normally, this is just a momentary push that delivers irrigation fluids for a couple of seconds. Thereafter, to remove the irrigation fluids and any body fluids, such as blood, puss, or any other types of fluids, the physician will push the vacuum button 70. The vacuum button 70 will switch the delivery line 14 from the delivering of saline solution from the IV bag 30 or 32 to the vacuum source 66 causing a vacuum to be created in the delivery line 14. Fluids will then be drawn from the patient 10 through the delivery line 14, cannula 12, the trumpet valve 60, and the vacuum line 62 to the vacuum cannister 64. The vacuum cannister 64 will collect any fluids therein with medical grade filters (not shown) preventing any of the fluids from reaching the vacuum source 66.

Figure 2:
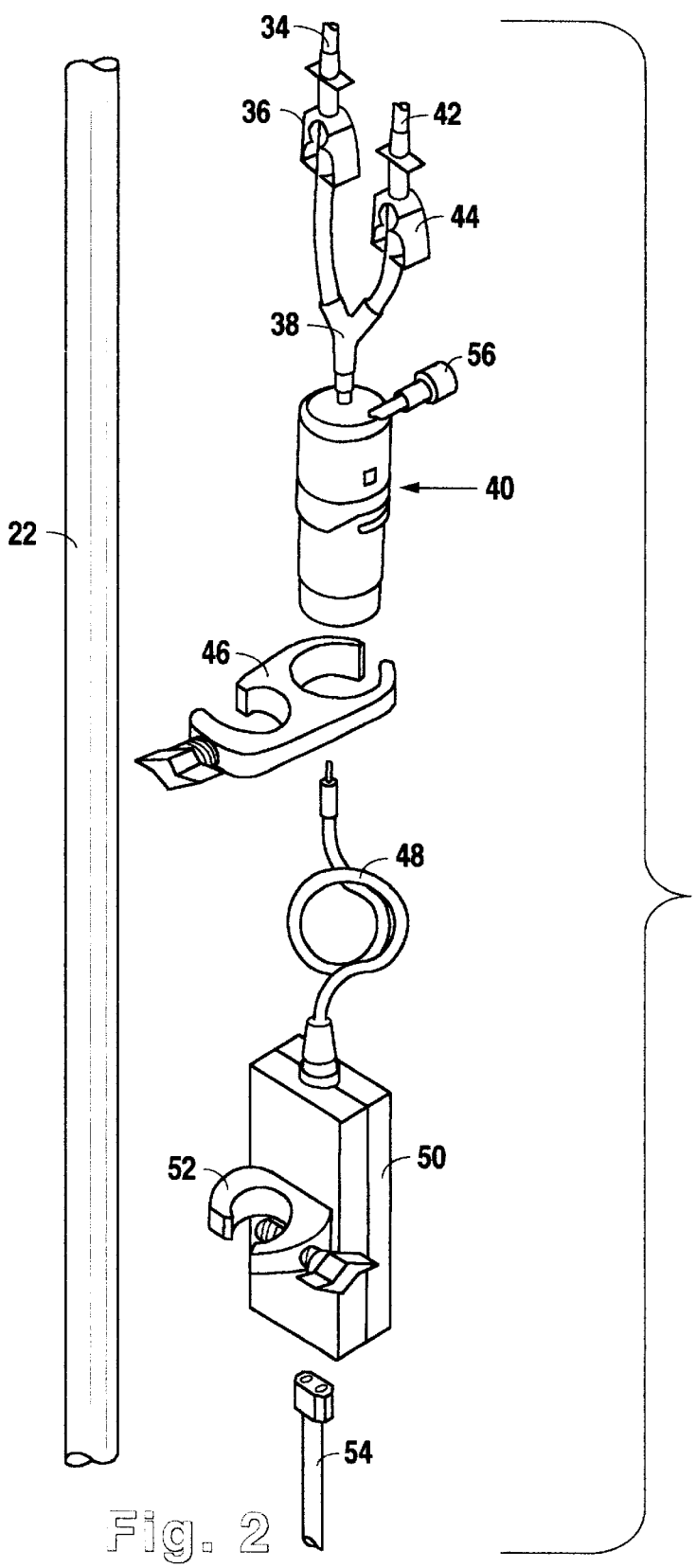
FIG. 2 is an enlarged, exploded, partial perspective view of a portion of the irrigation system.

Referring now to FIG. 2 of the drawings, there is shown an enlarged portion of a part of the irrigation system 16. The pump 40 is connected to the IV pole 22 by pump clamp 46 and to IV bag 30 (see FIG. 1) through Y connection 38, tubing clamp 36, and tube 34. Also, the pump 40 is connected to IV bag 32 via Y connection 38, tubing clamp 44, and tube 42. Normally, either tubing clamp 36 or tubing clamp 44 is open, but not both. This is so that the saline solution from either IV bag 30 or 32 can be used until it is essentially empty and then its respective tubing clamp 36 or 44 is closed with the other tubing clamp 44 or 36 opened. This allows for exchanging of the IV bags 30 or 32 without interruption of the laparoscopic surgery.

The pump 40 is connected through the power connection 48 to power supply 50. Power supply 50 is attached to the IV pole 22 by power supply clamp 52. While power supply 50 normally delivers 12 volts DC to the pump 40 during demands for irrigation fluids, power supply 50 actually converts normal AC current received through power cord 54 to a DC voltage.

Figure 3:
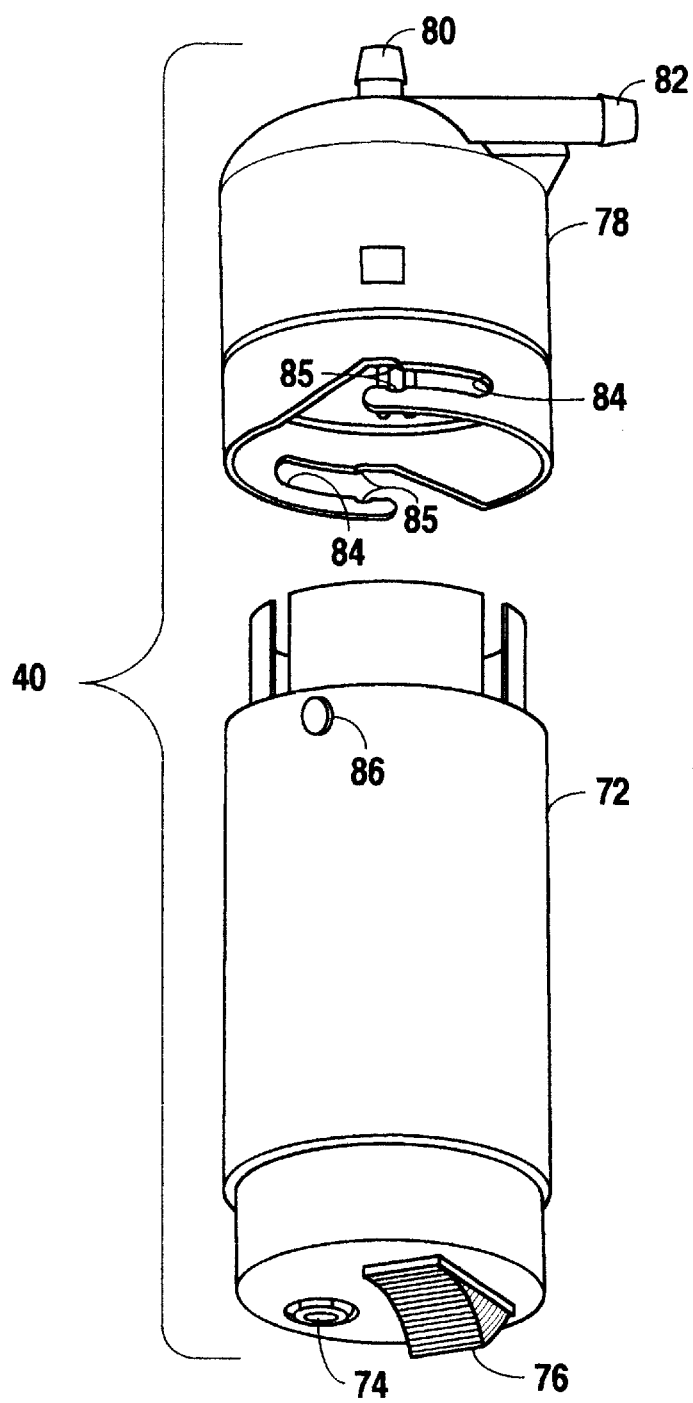
FIG. 3 is an exploded perspective view of a pump for use in the irrigation system during laparoscopic surgery.

Referring now to FIG. 3, an enlarged perspective view is shown of the pump 40. The motor 72 of the pump 40 has a power plug 74 for connection to power connection 48. An ON/OFF switch 76 is provided on the motor 72. The motor 72 is designed to be used again and again. The head 78 of the pump 40 is designed to be disposable. The head 78 is made of medical grade plastic and is connected at the top thereof by inlet fitting 80 to Y connection 38 (see FIG. 1). Outlet fitting 82 connects to the check valve 56 (see FIG. 1) to allow fluid flow to the patient 10.

To make the head 78 disposable, impellers (not shown) that are embodied within the disposable head 78 are also made of medical grade plastic. Slots 84 are provided in the lower portion of the disposable head 78 and are designed to match tabs 86 on the motor 72. By one simple twisting action, the tabs 86 lock into the slots 84 at indentations 85 with the disposable disposable head 78 being attached to the reusable motor 72. Therefore, hospital personnel by one simple twisting action can remove the disposable head 78 from the reusable motor 72. Thereafter, the disposable head 78 can be thrown away and another one inserted in place thereof. This does not require the use of hospital maintenance personnel and can be done by a member of the surgery team, such as a nurse. The disposable head 78 is made of medical grade plastics, but is much less expensive to replace than replacing the entire pump 40. By being able to continue to reuse the motor 72 of the pump 40, a substantial savings can occur between procedures. Internally between the disposable head 78 and the reusable motor 72 are mating shafts that have interlocking lugs and fingers (not shown) for ease of connection. The method and apparatus for coupling the mating shafts is the subject matter of a separate application filed by Gorman Rupp and is currently pending before the United States Patent and Trademark Office, though the serial number and the filing date are not currently known by applicant.

Figure 4:
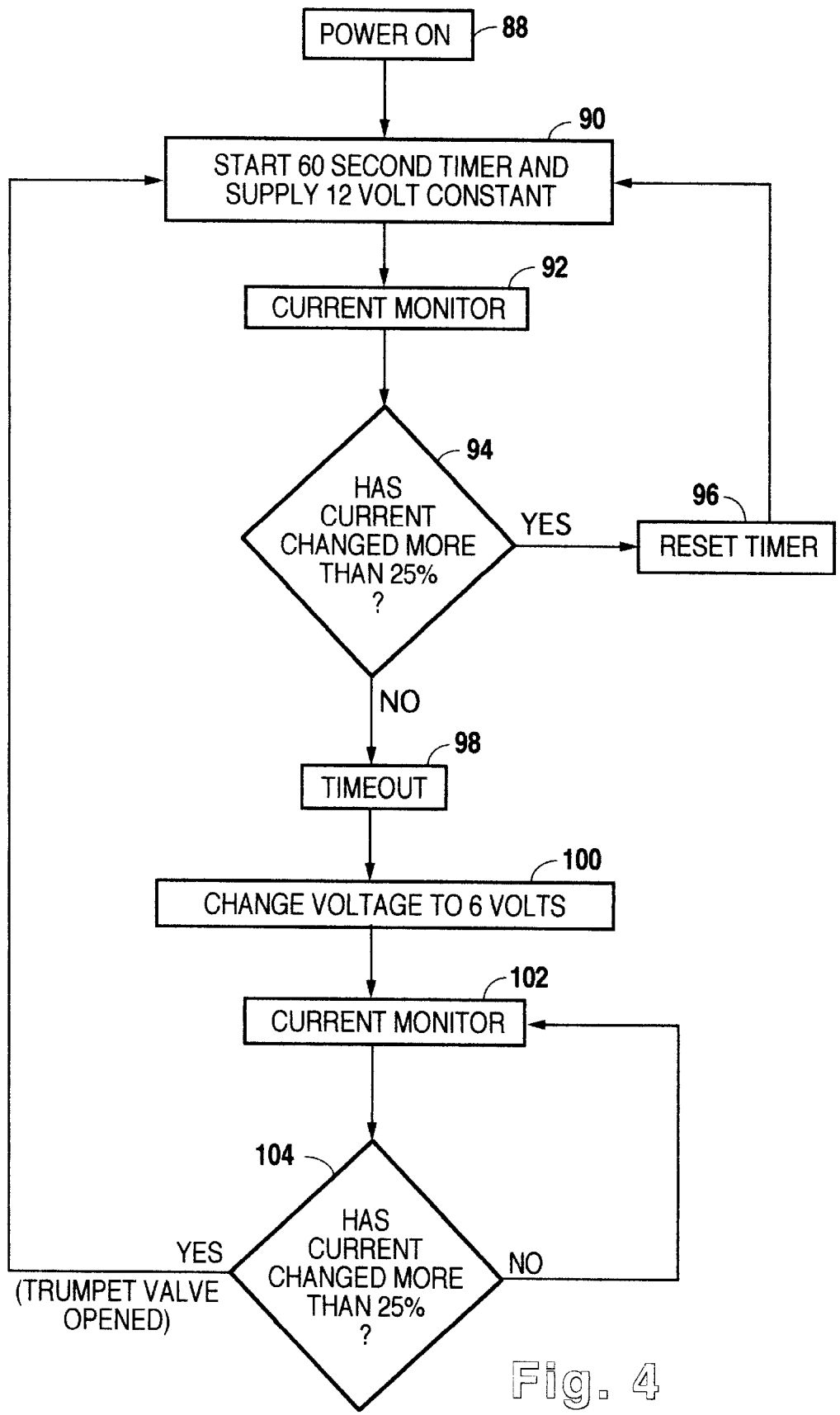
FIG. 4 is a flow diagram for the electronic controls of the pump for use in the irrigation system during laparoscopic surgery.

Contained within the power supply 50 is an electronic circuit that performs the function as indicated in FIG. 4. When power is turned ON to the power supply 50, such as plugging in the power cord 54, a power ON signal 88 is generated. The power ON signal 88 is fed to a timer 90. The timer 90 allows a constant 12 volt DC to be supplied, but starts a clock. In the preferred embodiment, the clock is a 60 second clock, but clearly other time periods can be utilized. During the 60 seconds, a current monitor 92 monitors the current being drawn by the pump 40 from the power supply 50. If at any time during the 60 seconds there is more than a 25 percent change in current, a "yes" signal is given by the "has current changed more than 25 percent" function 94. This results in a reset timer signal 96 being sent to the timer 90 to start the timing over again. If there has been no change in current by more than 25 percent as indicated by function 94, a "no" signal will be generated with a timed out signal 98 being generated. This will change the voltage being delivered by power supply 50 from 12 volts DC to 6 volts DC as indicated by function 100. Thereafter, there is a continual monitoring of current 102. If at any time the current changes by more than 25 percent as indicated by function 104, a "yes" signal is generated by function 104 to switch back to 12 volts DC and re-initiate the timer circuit 90. As long as there is no change, a "no" signal is generated by the "has current changed by more than 25 percent" function 104 and the current is continually monitored by current monitor 102.

While the preferred embodiment uses a 25% change in current, other percentages could be used to create the threshold condition.

What happens in actual practice is the physician may be performing endoscopic surgery and for extended periods of time makes no demand on the irrigation system 16. However, at such time as the surgeon pushes the irrigation button 68 of the trumpet valve 60, fluid will start flowing through the pump 40. This will cause the current to change by more than 25 percent, which will be detected by function 104 and generate a "yes" signal. The "yes" signal will instantaneously change the voltage being supplied from 6 volts DC back to 12 volts DC and restart the timer 90. Typically, the physician will make short bursts of irrigation fluid by pushing the irrigation button 68 of the trumpet valve 60. If the physician were to hold down the irrigation button 68 of the trumpet valve 60, it would drain the IV bag 30 or 32 in less than 60 seconds. Applicant knows of no occasion the physician would ever hold down the irrigation button 68 for that long.

On the other hand, if the physician has made a short request for irrigation fluid by pushing the irrigation button 68, and if that request has occurred within anytime in the last 60 seconds, full power of 12 volts DC would be provided to the pump 40. However, if the demand for irrigation has not occurred within the last 60 seconds, the voltage being provided to the pump 40 will be reduced from 12 volts DC to 6 volts DC. This allows the pump 40 to continue to run, but at a slower speed. The slower speed keeps the pressure maintained in the pump 40 for instantaneous delivery of IV fluid upon demand by the physician, but not at such a high speed as to create excess heat inside the pump 40. If the pump 40 was continually operated at 12 volts DC, but with no fluid flowing therethrough, which is referred to as a "deadhead" condition, the pump 40 would heat up to the point that it could cause the fluid to boil and even blow off the connections due to the internal pressures being built up in the fluid. The heat in the pump 40 would vaporize the fluid and create steam. If this hot fluid or steam was ever delivered to the patient 10, it also could cause internal burning of the patient 10. However, by reducing the voltage being provided to the pump 40 in half, it reduces almost exponentially the amount of heat being generated. At the lower voltage, there is no danger of creating undue heat in the pump 40.

Figure 5:
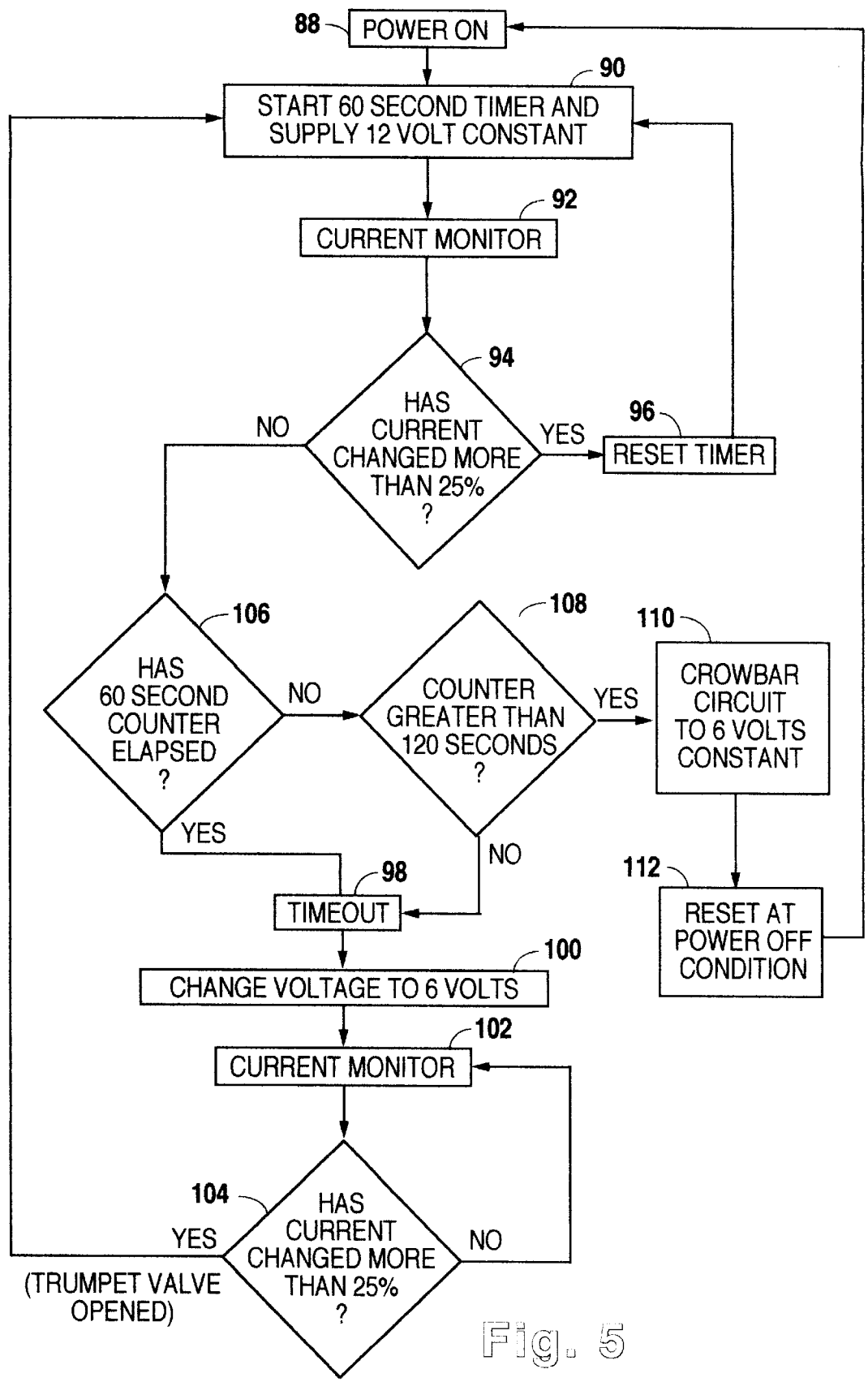
FIG. 5 is an alternative flow diagram for the electronic controls of the pump for use in the irrigation system during laparoscopic surgery.

For medical equipment used during surgery or other critical procedures, it may be desirable to have a failsafe circuit. In other words, if electronics were ever to fail, there is some type of redundant circuit that can take over. Therefore, while the electronic circuit as shown in FIG. 4 can perform the desired functions. FIG. 5 shows a functional block diagram that is identical to FIG. 4, but has the additional redundance circuit sometimes referred to as a "crowbar circuit." In FIG. 5, the same numerals for the same components as appear in FIG. 4 will be likewise numbered. Before the timed out function 98 has occurred, there is an additional "has 60 second counter elapsed?" monitor 106 included. If the answer is "no," then a counter greater than 120 seconds 108 is initiated. While 120 seconds is used in the preferred embodiment, other time periods could have been utilized as long as the second time period is longer than the first time period. If the counter greater than 120 seconds 108 is "no," the timed out function 98 is informed. If the answer to the counter greater than 120 seconds 108 is "yes," a crowbar circuit 110 is initiated. The crowbar circuit 110 initiates a signal to reset the entire circuit. A reset signal 112 is initiated that turns the power OFF in the power ON function 88.

In practice, if the electronics are not working properly, the crowbar circuit 110 will simply turn the power OFF in the electronics. An alternative approach may be to reset the power to 6 volts DC. In either event, the crowbar circuit 110 is overriding the other electronic portion of the circuit because it did not function properly. This is a failsafe type of condition that is beneficial in the medical industry.

Figure 6:
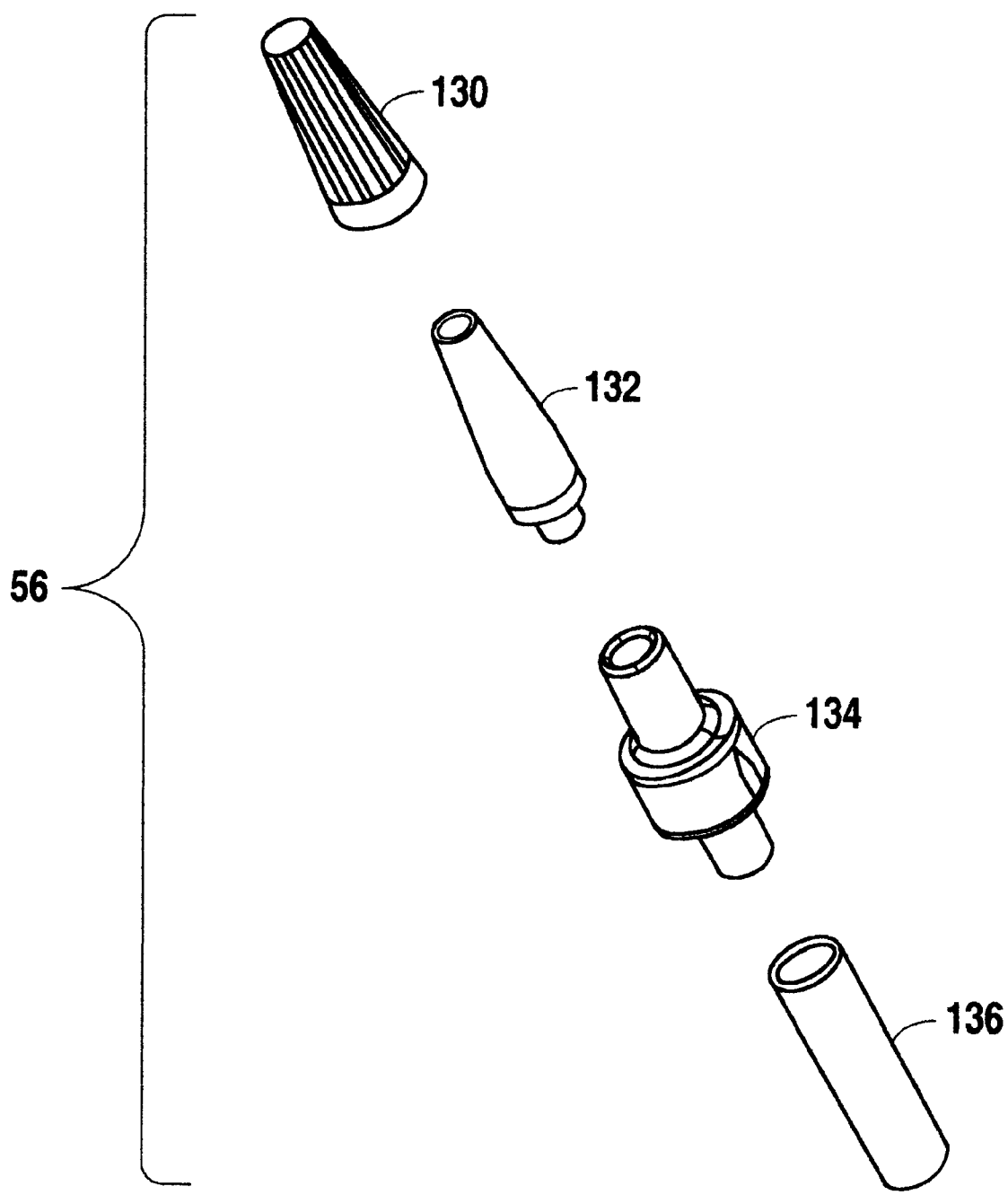
FIG. 6 is an exploded perspective view of the check valve used in an irrigation system for laparoscopic surgery.

Referring now to FIG. 6, there is an exploded view shown of the check valve 56 for the irrigation line 58 shown in FIG. 1. A cover 130, which may be removed and thrown away, is provided for the inlet end 132 of the check valve 56. The body portion 134 of the check valve 56 connects to the inlet end 132. An outlet tube 136 connects to the outlet side of the body portion 134 of the check valve 56. The outlet tube 136 may in fact be the irrigation line 58.

The check valve 56 is intended to reduce the possibility of contamination between patients. While the check valve 56 is a commercially available medical grade check valve, the disposable head 78 of the pump 40 is intended to be disposable after use in a single patient. However, it is also contemplated that the disposable head 78 can be used a few times before replacement with a new sterilized head 70. In this version, a plurality of check valves 56 may be provided in a kit with the system. The check valve 56 will prevent backwash from occurring from the patient 10 up to the disposable head 78 and thereby prevent contamination to the disposable head 78.

It should be understood that various modifications may be made to the embodiments described and shown herein. Therefore, the above description should not be construed as limiting, but merely as exemplifications of the preferred embodiments.

What is claimed is:

1. An irrigation system for use during endoscopic surgery on a patient comprising:
   a vacuum source;
   a source of irrigation fluid;
   a trumpet valve for alternately connecting said vacuum source or said irrigation fluid to said patient during said laparoscopic surgery according to demand by the user, a first button of said trumpet valve providing said irrigation fluid from said source to said patient, a second button of said trumpet valve providing suction from said vacuum source to said patient;
   a pump between said trumpet valve and said source of said irrigation fluid to continually provide said irrigation fluid under pressure to said trumpet valve during said laparoscopic surgery; and
   a vacuum cannister between said vacuum source and said trumpet valve to collect fluids or particles therein during said suction;
   said pump including a disposable head and a reusable motor with a quick disconnect therebetween.

2. The irrigation system for use during endoscopic surgery on the patient as recited in claim 1 further including control circuit between said pump and a power source, said control circuit reducing voltage being applied to said pump if demand for said irrigation fluid has not occurred for a first predetermined period of time.

3. The irrigation system for use during endoscopic surgery on the patient as recited in claim 2 wherein said control circuit includes an override portion, said override portion monitoring voltage delivered to said pump and if said monitoring voltage is not said reduced voltage after a second predetermined period of time of non-use, said monitoring voltage being overridden to provide said reduced voltage, said second predetermined period of time being longer than said first predetermined period of time.

4. The irrigation system for use during endoscopic surgery on the patient as recited in claim 1 comprises:
   an IV stand;
   two bags of IV fluid on said IV stand providing said source of said irrigation fluid; and
   Y-connection and tube clamps to connect only one of said two bags at a time to said disposable head of said pump.

5. The irrigation system for use during endoscopic surgery on the patient as recited in claim 4 having a check valve between said trumpet valve and said disposable head of said pump, said check valve preventing backwash from said patient to said disposable head.

6. A method of providing irrigation to a patient during endoscopic surgery consisting of the following steps:
   pressurizing an irrigation fluid by a pump to continually deliver pressurized irrigation fluid to a valve;
   periodically providing said pressurized irrigation fluid to said patient during said endoscopic surgery as demanded by the user at said valve;
   reducing voltage being delivered to said pump from a higher level to a lower level if there is no demand for said pressurized irrigation fluid for a first predetermined period of time, said lower level of said voltage being high enough to maintain said pressurized irrigation fluid at said valve; and
   increasing voltage being delivered to said pump back to said higher level when there is demand by the user for said pressurized irrigation fluid.

7. The method of providing irrigation to a patient during endoscopic surgery as recited in claim 6 includes a step of connecting a source of vacuum to said valve to continually provide suction at said valve, said periodical step also providing suction to said patient as demanded by the user.

8. The method of providing irrigation to a patient during endoscopic surgery as recited in claim 7 wherein said valve is a trumpet valve.

9. The method of providing irrigation to the patient during endoscopic surgery as recited in claim 6 including an override step to reduce voltage being delivered to said pump to said lower level, said override step monitoring said pump and if (a) there has been no demand for said pressurized irrigation fluid for a second predetermined period of time and (b) voltage being delivered to said pump is said higher level of said voltage, said voltage is automatically reduced to said lower of said level voltage, said second predetermined period of time being longer than said first predetermined period of time.

10. The method of providing irrigation to the patient during endoscopic surgery as recited in claim 6 includes between different endoscopic surgery procedures a step of removing a head of said pump from a motor thereof and replacing said head.

11. The method of providing irrigation to the patient during endoscopic surgery as recited in claim 8 includes a step of inserting a check valve between said pump and trumpet valve to prevent backwash, further steps include replacing said check valve between different laparoscopic surgery procedures.

12. The method of providing irrigation to the patient during endoscopic surgery as recited in claim 11 includes an additional step of periodically between different endoscopic surgery procedures a step of removing a head of said pump from a motor thereof and replacing said head.

13. The method of providing irrigation to the patient during endoscopic surgery as recited in claim 7 wherein said connecting to said source of vacuum is through a vacuum cannister.

14. The method of providing irrigation to the patient during endoscopic surgery as recited in claim 9 wherein said override step shuts OFF said pump.

* * * * *